(12) United States Patent
Benje et al.

(10) Patent No.: US 7,009,084 B2
(45) Date of Patent: Mar. 7, 2006

(54) METHOD FOR PRODUCING 1, 2-DICHLOROETHANE BY DIRECT CHLORINATION

(75) Inventors: Michael Benje, Darmstadt (DE); Dieter Jaculi, Burgkirchen (DE); Ingolf Mielke, Burgkirchen (DE); Peter Schwarzmaier, Kastl (DE); Klaus Krejci, Burghausen (DE); Joachim Schubert, Burghausen (DE); Horst Ertl, Pleiskirchen (DE)

(73) Assignees: Uhde GmbH, Dortmund (DE); Vinnolit Technologie GmbH & Co. KG, Burgkirchen (DE)

( * ) Notice: Subject to any disclaimer, the term of this patent is extended or adjusted under 35 U.S.C. 154(b) by 37 days.

(21) Appl. No.: 10/505,245

(22) PCT Filed: Feb. 1, 2003

(86) PCT No.: PCT/EP03/01000

§ 371 (c)(1),
(2), (4) Date: Dec. 16, 2004

(87) PCT Pub. No.: WO03/070673

PCT Pub. Date: Aug. 28, 2003

(65) Prior Publication Data

US 2005/0177011 A1    Aug. 11, 2005

(30) Foreign Application Priority Data

Feb. 21, 2002    (DE)    ................. 102 07 217

(51) Int. Cl.
C07C 17/02    (2006.01)

(52) U.S. Cl. ............................. 570/246; 570/231

(58) Field of Classification Search ............... 570/231, 570/246

See application file for complete search history.

(56) References Cited

U.S. PATENT DOCUMENTS

| 4,783,564 A * | 11/1988 | Piotrowski et al. | ......... 570/254 |
| 6,229,059 B1 * | 5/2001 | Motz | .......................... 570/247 |
| 6,252,125 B1 * | 6/2001 | Porscha | ..................... 570/246 |

FOREIGN PATENT DOCUMENTS

| DE | 199 10 964 A1 | 9/2000 |
| EP | 1 161 406 B1 | 12/2001 |
| GB | 1405926 | 9/1975 |

* cited by examiner

*Primary Examiner*—Johann Richter
*Assistant Examiner*—Chukwuma Nwaonicha
(74) *Attorney, Agent, or Firm*—Marshall & Melhorn, LLC

(57) ABSTRACT

The invention relates to a method for producing high purity 1,2-dichloroethane using a liquid reaction medium that is circulated and that is essentially composed of 1,2-dichloroethane and a catalyst. At least ethylene and chlorine are added to the reaction medium and a mainly chlorine-containing gas flow is dissolved in a part of the reaction medium which is essentially devoid of dissolved ethylene. The gaseous components not dissolved in this solution are removed from the solution by means of a gas-separation device and the solution from which the undissolved gas components were removed is contacted with ethylene which is present in dissolved form.

7 Claims, 1 Drawing Sheet

METHOD FOR PRODUCING 1, 2-DICHLOROETHANE BY DIRECT CHLORINATION

BACKGROUND OF THE INVENTION

The invention relates to a process for the production of 1,2-dichloroethane, hereinafter referred to as EDC, which primarily serves as an intermediate product in the production of monomer vinyl chloride, hereinafter referred to as VCM, which, in turn, is used to produce polyvinyl chloride (PVC). When EDC reacts to form VCM, hydrogen chloride (HCl) is obtained. Hence, EDC is preferably produced from ethylene ($C_2H_4$) and chlorine ($Cl_2$) in a manner such as to maintain a balance between the hydrogen chloride (HCl) produced and consumed in the various reactions, as represented by the following reaction equations:

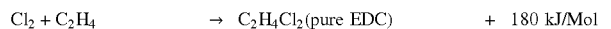
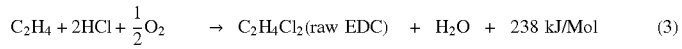

$Cl_2 + C_2H_4 \rightarrow C_2H_4Cl_2\text{(pure EDC)} + 180 \text{ kJ/Mol}$ (1)

$C_2H_4Cl_2\text{ (cracked EDC)} \rightarrow C_2H_3Cl\text{ (VCM)} + HCl - 71 \text{ kJ/Mol}$ (2)

$C_2H_4 + 2HCl + \frac{1}{2}O_2 \rightarrow C_2H_4Cl_2\text{(raw EDC)} + H_2O + 238 \text{ kJ/Mol}$ (3)

The process for the production of VCM with an adequate HCl balance—hereinafter referred to as "balanced VCM process"—comprises the following process steps:

direct chlorination in which one portion of the required EDC is produced from ethylene ($C_2H_4$) and chlorine ($Cl_2$) in the presence of a homogeneous catalyst and is made available as so-called pure EDC;

oxichlorination in which the remaining portion of the required EDC is produced from ethylene ($C_2H_4$), hydrogen chloride (HCl) and oxygen ($O_2$) and made available as so-called raw EDC;

fractionating EDC purification in which the raw EDC, together with the recycle EDC returned from the VCM fractionation step and, optionally, together with the pure EDC is freed from the secondary products formed in the oxichlorination and EDC pyrolysis steps in order to obtain a so-called feed EDC suitable for use in the EDC pyrolysis step; as an option, it is also possible to distil the pure EDC from the direct chlorination step in the heavy-ends column of the EDC distillation section;

EDC pyrolysis in which the feed EDC is thermally cracked, the mixture leaving the reactor, known as cracked gas, consisting of VCM, hydrogen chloride (HCl) and non-reacted EDC as well as secondary products;

VCM fractionation in which the desired pure VCM product is separated from the cracked gas while the other essential substances, viz. hydrogen chloride (HCl) and non-reacted EDC contained in the cracked gas, are separately recovered as valuable materials and returned as recycle HCl or recycle EDC to the balanced VCM process.

In most industrial processes, a circulating stream of EDC reaction product is used as the reaction fluid in direct chlorination. This can be accomplished in a loop-type reactor with external or internal circulation. The circulation can also be accomplished in a system with natural or forced circulation. In most cases ferric chloride is used as catalyst; in addition, sodium chloride which is able to inhibit the formation of heavy ends may be admixed as an additive. Oxygen, which is contained in minor quantities (approx. 0.5–1.5% by vol.) in the chlorine produced in the membrane electrolysis plant, or which can be admixed in the form of air to the chlorine upstream of the reactor, also has an inhibiting effect on the formation of secondary products.

The state of the art as regards direct chlorination is, for instance, described in DE 199 10 964 A1. The process according to DE 199 10 964 A1 aims at suppressing side reactions, especially the continuation of the chlorination process of EDC to 1,1,2-trichloroethane, by making most of the chlorination reaction take place in the homogeneous liquid phase. The ethylene, which is less readily soluble in EDC than chlorine, is completely dissolved in the main stream of the circulating EDC reaction fluid in a co-current bubble column. The chlorine, which is more readily soluble in EDC than ethylene, is dissolved in a supercooled EDC part-stream and the resulting solution of chlorine in EDC is fed to the circulating main stream which already contains the dissolved ethylene. The reaction (1) in the downstream largely homogenous reaction zone takes place very rapidly. It was found, however, that gaseous constituents (inerts) contained in the chlorine in admixed form as well as the oxygen from the membrane electrolysis cells were not completely dissolved in the EDC in the reaction zone but they were present in the form of fine gas bubbles causing the formation of a phase interface. This interface is seemingly able to facilitate the formation of secondary products. The secondary products obtained were primarily monochloroacetaldehyde, dichloroacetaldehyde and trichloroacetaldehyde (chloral) which cannot be separated from the EDC or only with difficulty and tend to cause problems in the downstream process steps. The formation of 1,1,2-trichloroethane was also observed. It was not known formerly that the formation of a phase interface is connected with the formation of secondary products. In the state of the art even processes are described where the formation of a phase interface is absolutely necessary. In this context it is referred to the U.S. Pat. No. 4,783,564 where some data to the required density of dissipation of energy can be found.

SUMMARY OF THE INVENTION

It is therefore the aim of the present invention to prevent the formation of an interface that promotes side reactions in the reaction zone and to provide an economical process for the production of high-purity EDC.

The invention can achieve the aim as follows:

A gas stream with chlorine as the main constituent is dissolved in part of the reaction fluid, which is essentially free of dissolved ethylene, the gaseous constituents which have not been dissolved in this solution are removed from the solution by means of a centrifugal gas separator as device for gas separation and the solution, which has been freed from non-dissolved gas constituents, is then brought into contact with solute ethylene supplied for this purpose.

The described procedure influences the reaction conditions in that the formation of a gas/liquid interface, which would catalyse the formation of secondary products, especially 1,1,2-tetrachloroethane, is prevented in the zone where the main reaction takes place. The portion of high ends, including especially oxygen compounds resulting from the presence of residual inert constituents in the reaction zone is thus eliminated, a feature which improves the product quality and represents an advantage of the present invention.

An economic advantage also results from the significant reduction of the amount of reactor waste gas. For safety reasons, the reaction is usually run with an excess of ethylene. The excess ethylene as well as the oxygen and inert portions contained in the chlorine will be found again in the waste gas stream of the plant after the product has been separated by condensation. To prevent the formation of an explosive gas mixture in the waste gas system, it is necessary to add nitrogen to the reactor waste gas for the purpose of rendering it inert. The elimination of the non-dissolved gas constituents, especially the oxygen usually contained therein, will reduce the need for rendering inert with nitrogen. Hence the waste gas has not only been freed from the non-dissolved gas constituents which have been removed by the gas separator but it also contains a lower portion of inert gas since the latter is no longer required to the previous extent. Normally, the waste gas from a plant for the production of EDC by the balanced process is fed to an incineration plant. As such incineration plants are characterised by high equipment costs incurred on account of special materials and as the capacity of such plants depends to a large extent on the quantity of waste gas from the direct chlorination reactor, a reduction of the amount of waste gas will result in considerable cost savings.

The invention also relates to a number of embodiments for the treatment of the gaseous constituents removed by the gas separator. The following options may be applied individually or in parallel, the decision being up to the specialist engineer in consideration of the local circumstances and the exploitation of the plant.

According to an embodiment of the present invention, at least part of the gaseous constituents that have been removed from the chlorine-bearing solution by the gas separator are admixed to the reaction fluid at a point of the reaction section, the reactor or a dissolving device, in which the reaction of chlorine with ethylene for forming 1,2-dichloroethane has almost terminated or can no longer take place.

It is of special advantage to admix the gaseous constituents removed from the chlorine-bearing solution by the gas separator to the reaction fluid downstream of the reaction section in which the chlorine reacts with the ethylene to yield 1,2-dichloroethane.

Since the reaction of the ethylene is almost complete at the feed point of the oxygen and the inerts, the ethylene is no longer available as precursor for the formation of oxygen compounds. Thus, the portion of oxygen compounds for which the ethylene serves as a precursor is also eliminated so that a further increase in product quality is achieved and represents another advantage of the present invention.

In another embodiment of the process, at least part of the gaseous constituents removed from the chlorine-bearing solution by means of the gas separator are fed to a facility for secondary reaction, this facility being operated at a lower temperature than applied to the main reaction.

In another embodiment of the process, at least part of the gaseous constituents removed from the chlorine-bearing solution by means of the gas separator are fed to a facility for the incineration of residues without further rendering inert.

In another embodiment of the process, at least part of the gaseous constituents removed from the chlorine-bearing solution by means of the gas separator are fed to a chlorination facility.

It is of special advantage to pipe such a part-stream to a chlorination facility in which light ends from a plant for the production of VCM from EDC by reaction (2), so-called recycle EDC, are converted to heavy ends.

The process according to the present invention may be operated with any known type of gas separator which is able to separate fine bubbles. The use of a centrifugal gas separator as applied in instrumentation engineering has proved to be of special advantage.

BRIEF DESCRIPTION OF THE DRAWINGS

The invention is illustrated in more detail by means of the following example.

DESCRIPTION OF THE PREFERRED EMBODIMENT

Figure 1:
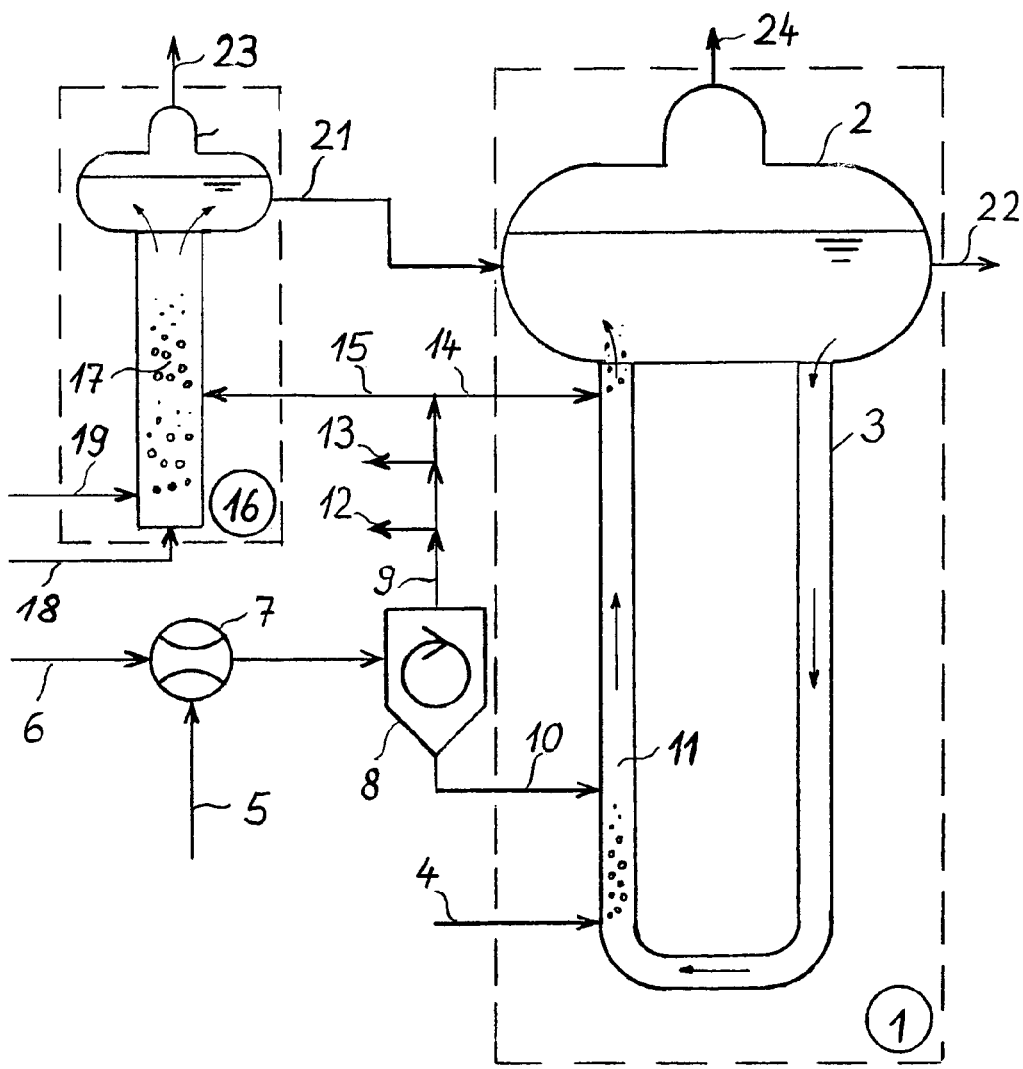
FIG. 1 shows a direct chlorination reactor 1 consisting of a degassing vessel 2 and a loop 3 in which the reaction (1) takes place, as well as the gas separator in accordance with the present invention and its embodiments.

Ethylene 4, which is less readily soluble than chlorine, is fed to the EDC circulating in loop 3 where it dissolves completely. Gaseous chlorine 5, which is more readily soluble in EDC, is dissolved in a supercooled EDC part-stream 6 by means of an injector nozzle 7. Centrifugal gas separator 8 is arranged downstream of injector nozzle 7 for separating the gaseous phase left over from the dissolution of the chlorine and consisting of oxygen, inert gases and the partial-pressure-related portions of chlorine and EDC from the liquid phase, and it then discharges it as tail gas 9. The resulting homogenous solution 10 of chlorine in EDC is transferred to reaction zone 11 in loop 3 where the rapid homogenous chlorination of the ethylene to form 1,2-dichloroethane takes place.

The tail gas stream is then divided into 4 part-streams:

Part-stream 12 is fed to an incineration facility, part-stream 13 is fed to a facility for the chlorination of recycle EDC, part-stream 14 is fed to the direct chlorination reactor 1 and part-stream 15 is fed to a facility for secondary reaction 16.

The facility for secondary reaction 16 mainly consists of a short secondary reaction section 17 operated with supercooled EDC 18 packed with catalyst, which receives part-stream 15 as well as a minor ethylene stream 19. The liquid EDC stream 21 passes through secondary reaction section 17 and degassing device 20 and is then fed to direct chlorination reactor 1 from which it leaves the plant as EDC product 22 together with the EDC obtained there. The waste gas 23 freed from chlorine in degassing device 20 is fed to an incineration facility. In contrast to the EDC vapour/waste gas mixture 24, the chlorine-free waste gas 23 contains only a small quantity of EDC which would have to be removed. As the facility for secondary reaction 16 can be operated under very favourable conditions, i.e. low feed rate, low temperature, consequently a higher ethylene solubility and, as a result of the low temperature, a considerably reduced drift to form secondary products, it is possible to achieve a significant reduction of the amount of waste gas and an improvement of the EDC purity.

LEGEND

1 Direct chlorination reactor
2 Degassing vessel
3 Loop
4 Ethylene
5 Chlorine
6 EDC part-stream
7 Injector nozzle
8 Centrifugal gas separator
9 Tail gas
10 Homogeneous solution
11 Reaction zone
12 Part-stream
13 Part-stream
14 Part-stream
15 Part-stream
16 Facility for secondary reaction
17 Secondary reaction section
18 Supercooled EDC
19 Ethylene stream
20 Degassing device
21 EDC stream
22 EDC product
23 Chlorine-free waste gas
24 EDC vapour/waste gas mixture

What is claimed is:

1. A process for the production of high-purity 1,2-dichloroethane using a circulating stream of liquid reaction fluid which mainly consists of 1,2-dichloroethane and a catalyst, in which at least ethylene and chlorine are admixed to the reaction fluid, wherein a gas stream with chlorine as the main constituent is dissolved in a portion of the reaction fluid, which is essentially free of dissolved ethylene, the gaseous constituents non-dissolved in this solution, being removed from the said solution by means of a centrifugal gas separator as device for gas separation and the solution freed from non-dissolved gas constituents being brought into contact with solute ethylene supplied for this purpose.

2. The process according to claim 1, wherein at least part of the gaseous constituents that have been removed from the chlorine-containing solution by the gas separator are admixed to the reaction fluid at a point of the reaction section, the reactor or a dissolving device, in which the reaction of chlorine with ethylene for forming 1,2-dichloroethane has almost terminated or can no longer take place.

3. The process according to claim 2, wherein the gaseous constituents which have been removed from the chlorine-bearing solution by the gas separator are admixed to the reaction fluid downstream of the reaction section in which the chlorine reacts with the ethylene to yield 1,2-dichloroethane.

4. The process according to claim 1, wherein at least part of the gaseous constituents removed from the chlorine-bearing solution by means of the gas separator are fed to a facility for secondary reaction, this facility being operated at a lower temperature than applied to the main reaction.

5. The process according to claim 1, wherein at least part of the gaseous constituents removed from the chlorine-bearing solution by means of the gas separator are fed to a facility for the incineration of residues without rendering inert.

6. The process according to claim 1, wherein at least part of the gaseous constituents removed from the chlorine-bearing solution by means of the gas separator are fed to a chlorination facility.

7. The process according to claim 6, wherein the chlorination facility serves to convert light ends from a plant for monomer vinyl chloride production from 1,2-dichloroethane to heavy ends.

* * * * *